United States Patent
Hyung et al.

(10) Patent No.: US 9,724,061 B2
(45) Date of Patent: Aug. 8, 2017

(54) X-RAY IMAGING APPARATUS AND METHOD OF CONTROLLING THE SAME

(71) Applicant: Samsung Electronics Co., Ltd., Suwon-Si, Gyeonggi-Do (KR)

(72) Inventors: Seung Yong Hyung, Yongin-si (KR); Ji Yeun Kim, Seoul (KR); Kyung Shik Roh, Seongnam-si (KR); Jong Won Lee, Uiwang-si (KR); Ju Suk Lee, Hwaseong-si (KR); Won Jun Hwang, Seoul (KR); Hyo Seok Hwang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 207 days.

(21) Appl. No.: 14/498,554

(22) Filed: Sep. 26, 2014

(65) Prior Publication Data

US 2015/0139382 A1 May 21, 2015

(30) Foreign Application Priority Data

Nov. 18, 2013 (KR) ........................ 10-2013-0140234

(51) Int. Cl.
*A61B 6/00* (2006.01)
*A61B 6/06* (2006.01)
(Continued)

(52) U.S. Cl.
CPC ............... *A61B 6/469* (2013.01); *A61B 6/06* (2013.01); *A61B 6/12* (2013.01); *A61B 6/405* (2013.01);
(Continued)

(58) Field of Classification Search
CPC ......... A61B 6/587; A61B 6/542; A61B 6/547; A61B 6/12
See application file for complete search history.

(56) References Cited

U.S. PATENT DOCUMENTS 5,369,678 A * 11/1994 Chiu ....................... A61B 6/542
378/62
2006/0126911 A1 6/2006 Bohm et al.
(Continued)

FOREIGN PATENT DOCUMENTS

DE 10 2009 015 830 A1 10/2010
JP 2004-209239 A 7/2004
(Continued)

OTHER PUBLICATIONS

European Search Report mailed on Mar. 27, 2015.
Decision on Grant mailed on Jun. 17, 2016 for corresponding European Patent Application No. 14 191 242.8-1666.

*Primary Examiner* — Hoon Song
(74) *Attorney, Agent, or Firm* — Harness, Dickey & Pierce P.L.C.

(57) ABSTRACT

Provided are an X-ray imaging apparatus that is capable of tracking a position of an object of interest using a Kalman filter so as to reduce the amount of X-ray radiation exposure of a subject, calculating covariance indicative of accuracy of the tracing, and controlling a collimator so that the position of the object of interest and calculated covariance may be correlated with a position and an area of a region into which X-rays are radiated, and a method of controlling the X-ray imaging apparatus.

18 Claims, 16 Drawing Sheets

(51) Int. Cl.
*A61B 6/12* (2006.01)
*A61B 34/20* (2016.01)
*A61B 90/00* (2016.01)

(52) U.S. Cl.
CPC .............. *A61B 6/481* (2013.01); *A61B 6/482* (2013.01); *A61B 6/486* (2013.01); *A61B 6/503* (2013.01); *A61B 6/504* (2013.01); *A61B 6/5211* (2013.01); *A61B 6/542* (2013.01); *A61B 6/4441* (2013.01); *A61B 6/487* (2013.01); *A61B 6/547* (2013.01); *A61B 2034/2046* (2016.02); *A61B 2090/376* (2016.02)

(56) References Cited

U.S. PATENT DOCUMENTS

| | | | |
|---|---|---|---|
| 2007/0270686 | A1 | 11/2007 | Ritter et al. |
| 2008/0287783 | A1* | 11/2008 | Anderson ................ A61B 5/06 600/429 |
| 2009/0062641 | A1 | 3/2009 | Barbu et al. |
| 2009/0225944 | A1 | 9/2009 | Lee et al. |
| 2011/0170662 | A1 | 7/2011 | Baumgart |
| 2012/0296202 | A1 | 11/2012 | Mountney et al. |
| 2013/0030286 | A1 | 1/2013 | Alouani et al. |
| 2013/0072787 | A1* | 3/2013 | Wallace .................. A61B 6/12 600/424 |
| 2014/0112438 | A1* | 4/2014 | Mountney ................ A61B 6/12 378/62 |

FOREIGN PATENT DOCUMENTS

| | | |
|---|---|---|
| KR | 20120002359 A | 1/2012 |
| WO | WO-2012-123850 A1 | 9/2012 |
| WO | WO-2014-162275 A1 | 10/2014 |

* cited by examiner

X-RAY IMAGING APPARATUS AND METHOD OF CONTROLLING THE SAME

CROSS-REFERENCE TO RELATED APPLICATION

This application claims priority from Korean Patent Application No. 10-2013-140234, filed on Nov. 18, 2013 in the Korean Intellectual Property Office, the disclosure of which is incorporated herein by reference in its entirety.

BACKGROUND

1. Field

Example embodiments relate to an X-ray imaging apparatus that is configured to image an internal structure of a subject by radiating X-rays onto the subject, and/or a method of controlling the same.

2. Description of the Related Art

X-ray imaging apparatuses are apparatuses that are typically configured to obtain an image inside a subject by radiating X-rays onto the subject and using the X-rays transmitted by the subject. Since transmittance of X-rays varies according to, for example, the characteristics of a material used to form the subject, an internal structure of the subject can be imaged by detecting intensity or strength of the X-rays transmitted by the subject.

Currently, X-ray moving image technology has been developed to observe movement in the subject and has been used in the field of X-ray imaging, for example during an intervention surgical procedure such as angiography, or fluoroscopy.

It is typically desirable to reduce a radiation dose of the X-rays radiated onto the subject so as to ensure the safety of the X-ray imaging apparatuses, and research and development has been conducted so as to reduce the radiation dose of the X-rays.

However, when a method of reducing the radiation dose of the X-rays disturbs a workflow of procedure, or becomes a complicated process for the X-Ray operator, the operator may not prefer a reduction in the radiation dose of the X-rays and prefer instead a smoother or simpler surgical procedure.

SUMMARY

Example embodiments relate to an X-ray imaging apparatus that is configured to track a position of an object of interest using a Kalman filter, to calculate covariance indicative of accuracy of the tracking, and to control a collimator so that the position of the object of interest and calculated covariance may be correlated with a position and an area of a region into which X-rays are radiated, and/or a method of controlling the X-ray imaging apparatus.

Additional example embodiments will be set forth in part in the description which follows and, in part, will be obvious from the description, or may be learned by practice of the example embodiments.

In accordance with at least one example embodiment, an X-ray imaging apparatus includes an X-ray source, a collimator configured to adjust a radiation region of X-rays radiated by the X-ray source and a processor configured to determine a region of interest (ROI) in an X-ray image, to trace or track a position of an object of interest in the ROI, and to control the collimator so that a region in which the X-rays are radiated is correlated with tracing or tracking the object of interest.

In accordance with at least one example embodiment, a method of controlling an X-ray imaging apparatus, includes determining a region of interest (ROI) in an X-ray image, tracking a position of an object of interest in the ROI and controlling a collimator so that a region in which X-rays are radiated, is correlated with tracking the object of interest. In accordance with still another example embodiment, an X-ray imaging apparatus includes an X-ray source, a collimator configured to adjust a radiation region of X-rays radiated by the X-ray source, a processor configured to determine a region of interest (ROI) in an X-ray image, to track a position of the object of interest in the ROI, and to calculate covariance indicative of accuracy of the tracking, and a controller configured to control driving of the collimator to correlate a position of a region in which X-rays are radiated, to follow the traced position of the object of interest and a size of the region in which the X-rays are radiated, is correlated with the covariance.

Example embodiments include developing technology for reducing the radiation dose of X-rays radiated onto a subject without disturbing the X-ray operator's surgical procedure.

At least one example embodiment relates to a computer-implemented method of X-ray imaging including adjusting a radiation of X-rays radiated by an X-ray source via the processor, determining a region of interest (ROI) in an X-ray image, tracking a position of an object of interest in the ROI, and correlating a region in which the X-rays are radiated with the tracked position of the object of interest.

BRIEF DESCRIPTION OF THE DRAWINGS

These and/or other example embodiments will become apparent and more readily appreciated from the following description, taken in conjunction with the accompanying drawings of which.

DETAILED DESCRIPTION

Figure 1:
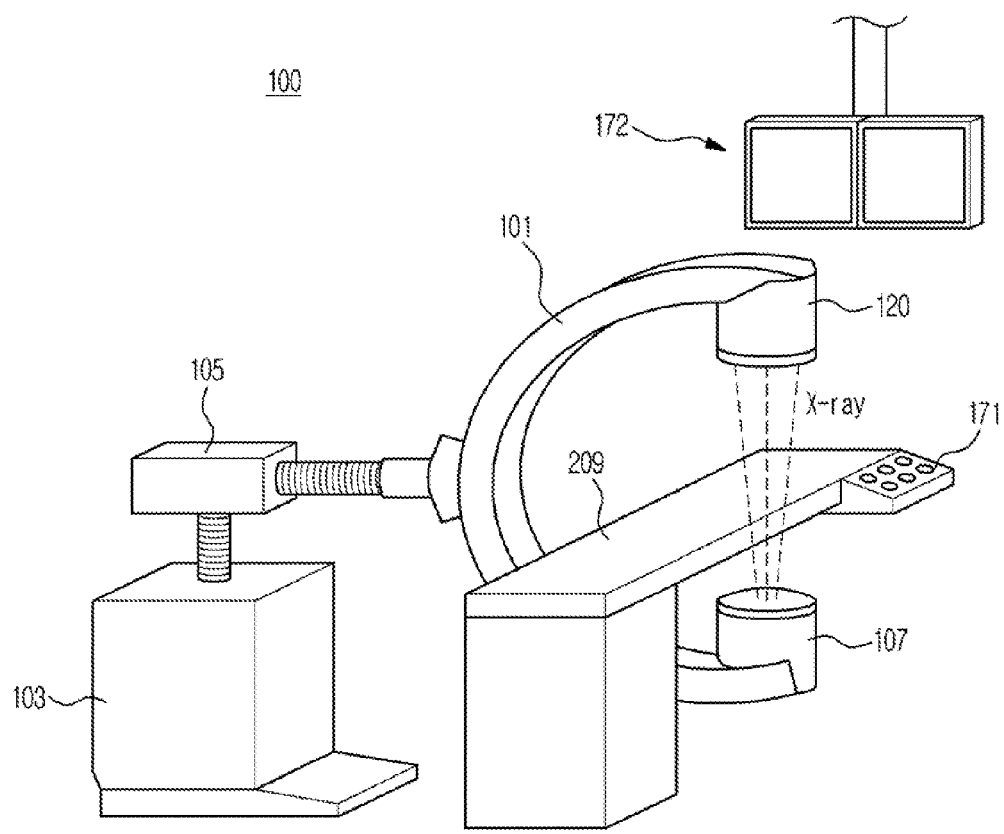
FIG. 1 illustrates an X-ray imaging apparatus in accordance with at least one example embodiment.

Reference will now be made in detail to the example embodiments illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures. Expressions such as "at least one of," when preceding a list of elements, modify the entire list of elements and do not modify the individual elements of the list.

The following example embodiments are not to restrict or limit the scope thereof. It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

In the drawing figures, the dimensions of layers and regions may be exaggerated for clarity of illustration. Like reference numerals refer to like elements throughout. The same reference numbers indicate the same components throughout the specification.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain example embodiments of the present description.

Figure 2:
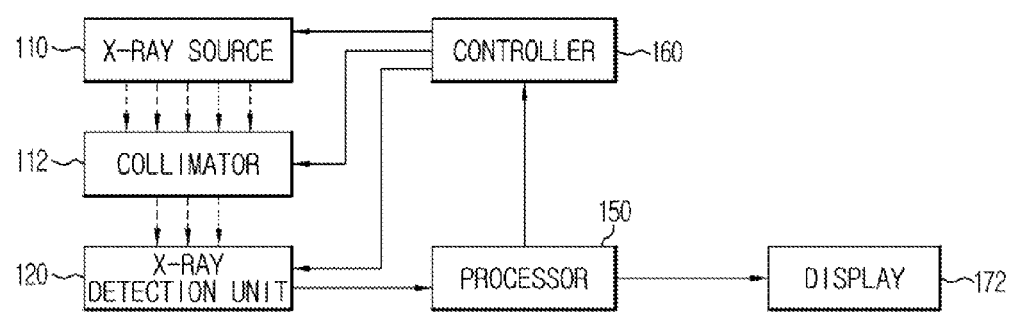
FIG. 2 is a block diagram of the example X-ray imaging apparatus illustrated in FIG. 1.
Figure 3:
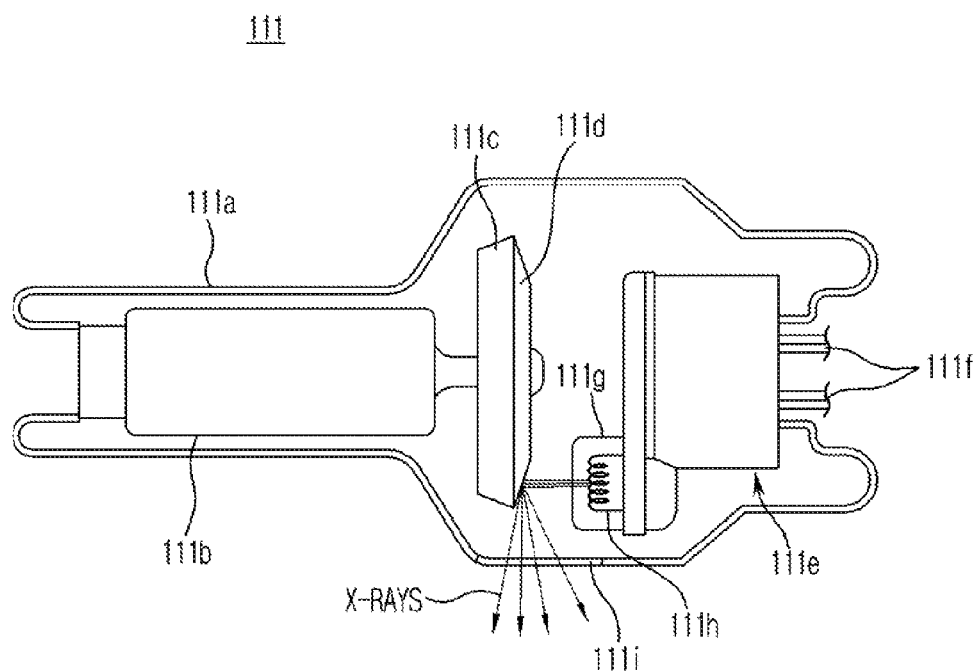
FIG. 3 is a cross-sectional view illustrating an internal structure of an X-ray tube included in the example X-ray imaging apparatus of FIG. 1.

FIG. 1 illustrates an X-ray imaging apparatus in accordance with at least one example embodiment, FIG. 2 is a block diagram of the X-ray imaging apparatus illustrated in FIG. 1, and FIG. 3 is a cross-sectional view illustrating an internal structure of an X-ray tube included in the example X-ray imaging apparatus of FIG. 1.

As illustrated in FIG. 1, an example X-ray imaging apparatus 100 for angiography may have a structure of a C-arm 101. An X-ray generation assembly 107 and an X-ray detection unit 120 may be mounted on both ends of the C-arm 101. The C-arm 101 may be connected to a body 103 via a connection shaft 105 and may rotate in an orbital direction.

As illustrated in FIG. 2, an X-ray source 110, a collimator 112, and a filtering unit (not shown) may be provided inside the X-ray generation assembly 107 of FIG. 1. If a patient table 209 is placed between the X-ray generation assembly 107 and the X-ray detection unit 120 and a subject is placed on the patient table 209, the X-ray source 110 radiates X-rays onto the subject, and the X-ray detection unit 120 detects the radiated X-rays from or through the subject, thereby obtaining an X-ray image of the subject.

The X-ray imaging apparatus 100 for angiography may perform X-ray imaging according to various imaging modes and may obtain a real-time moving image regarding the subject. A user may perform a surgical procedure or diagnosis while watching a display 172 that includes, for example, one screen or a plurality of screens and that may display one image or several images required for a given surgical procedure or diagnosis.

The user may input necessary information using an input unit 171 provided on the X-ray imaging apparatus 100. For example, the user may input a period or frequency at the input unit 171 so that the X-ray source 110 may radiate the X-rays repeatedly according to the inputted frequency. The input period may be transmitted to a controller 160 illustrated in FIG. 2, and the controller 160 may control the X-ray source 110 according to the input period.

FIG. 2 is a block diagram of the example X-ray imaging apparatus 100 illustrated in FIG. 1. The configuration of the X-ray imaging apparatus 100 will be described with reference to FIG. 2 in more detail. Referring to FIG. 2, the X-ray imaging apparatus 100 includes the X-ray source 110 that is configured to generated and radiate X-rays, a collimator 112 that is configured to adjust a radiation range of the X-rays radiated by the X-ray source 110, the X-ray detection unit 120 that is configured to detect the X-rays transmitted by the subject and to obtain frame data, a processor 150 that is configured to trace an object of interest of a region of interest (ROI) and to output a signal used to control driving of the collimator 112 so that the X-ray radiation region may be controlled while interlocking or correlating with tracing, the controller 160 that is configured to set parameters for X-ray imaging and to control driving of the collimator 112 according to the signal output by the processor 150, and the display 172 that includes one screen or a plurality of screens and that may display one image or several images used for the surgical procedure or diagnosis. According to at least one example embodiment, the processor 150 may be in the X-ray imaging apparatus 100, for example in the X-ray detection unit 120 or at the input unit 171. The processor 150 may also be coupled to the X-ray imaging apparatus 100, for example coupled to the X-ray detection unit 120 or to the input unit 171. According to at least one example embodiment, the controller 160 may be in the X-ray imaging apparatus 100, for example in the X-ray generation assembly 107. The controller 160 may also be coupled to the collimator 112.

According to at least one example embodiment, during operation of the X-Ray imaging apparatus, the X-ray source 110 generates the X-rays and radiates the X-rays onto the subject. The X-ray source 110 generates the X-rays using power supplied by a power supply unit (not shown). The energy of the X-rays may be controlled by at least one of a tube voltage and a filter, and the intensity or radiation dose of the X-rays may be controlled by a tube current and an X-ray exposure time. The X-ray source 110 includes an X-ray tube 111, illustrated in FIG. 3, that generates the X-rays.

FIG. 3 illustrates a configuration of the X-ray tube 111, according to at least one example embodiment. Referring to FIG. 3, the X-ray tube 111 may be implemented with a two-pole vacuum tube including an anode 111c and a cathode 111e, wherein a tube body may be a glass bulb 111a formed of silicic acid hard glass.

According to at least one example embodiment, the cathode 111e includes a filament 111h and a focusing electrode 111g that focuses electrons. The focusing electrode 111g is also referred to as a focusing cup. The inside of the glass bulb 111a is in a high vacuum state of about 10 mmHg, and the cathode filament 111h is heated to a high temperature, thereby generating thermoelectrons.

A tungsten (W) filament may be used as the filament 111h, and the filament 111h may be heated by applying currents to electrical conducting wires 111f connected to the filament 111h. However, example embodiments are not limited to employing of the filament 111h in the cathode 111e, and carbon nanotubes that may be driven with a high speed pulse may also be used as the cathode 111e.

The anode 111c may be mainly formed of copper (Cu), and a target material 111d may be applied or formed at a side facing the cathode 111e. For example, the target material 111d may be a high resistance material, such as chromium (Cr), iron (Fe), cobalt (Co), nickel (Ni), tungsten (W), and/or molybdenum (Mo). The higher the melting temperature of the target material 111d, the smaller a focal spot size.

When a high voltage is applied between the cathode 111e and the anode 111c, the thermoelectrons generated in the filament 111h are accelerated, collide with the target material 111d of the anode 111c, and generate X-rays as a result. The generated X-rays may be radiated to the outside through a window 111i, and the window 111i may be, for example, a beryllium (Be) thin film.

The target material 111d may be rotated by a rotor 111b. When the target material 111d is rotated, thermal accumulation may be increased by 10 times or more per unit area, and the focal spot size may be reduced compared to the case in which the target material 111d is fixed.

A voltage applied between the cathode 111e and the anode 111c of the X-ray tube 111 is referred to as a tube voltage, and the size of the tube voltage may be indicated by a peak value kVp. When the tube voltage increases, the speed of the thermoelectrons increases. If the speed of the thermoelectrons increases, the energy (photon energy) of the X-rays generated while colliding with the target material 111d may be increased.

Also, a filter may be disposed in a radiation direction of the X-rays so as to control the outgoing energy of the X-rays. A filter that filters the X-rays in a particular wavelength band may be disposed at a front side or rear side of the window 111i, and the filter may filter the X-rays in, for example, a particular energy band. For example, if a filter formed of aluminum or copper is disposed, the X-rays in a low energy band are filtered so that the energy of the radiated X-rays increases, or only the X-rays having a higher energy band are emitted.

A current that flows through the X-ray tube 111 is referred to as a tube current, and the size of the tube current may be indicated by an average value mA. If the tube current increases, the radiation dose (the number of X-ray photons that collide with the target 111d) of the X-rays increases.

Energy bands of the X-rays may be controlled by adjusting the tube voltage, and strengths and radiation doses of the X-rays may be controlled by adjusting the tube current and the X-ray exposure time. Thus, the energy bands or strengths of the radiated X-rays may be controlled by adjusting the tube voltage or the tube current according to the type or characteristics of the subject, according to at least one example embodiment.

The example X-ray source 110 generates the X-rays using the above-described X-ray tube 111 and radiates the generated X-rays onto the subject.

When the X-rays are radiated onto the subject by the X-ray source 110, a degree of X-ray attenuation may vary according to one or more types of tissue or material present inside the body of the subject, and according to the energy bands of the radiated X-rays.

Figure 4:
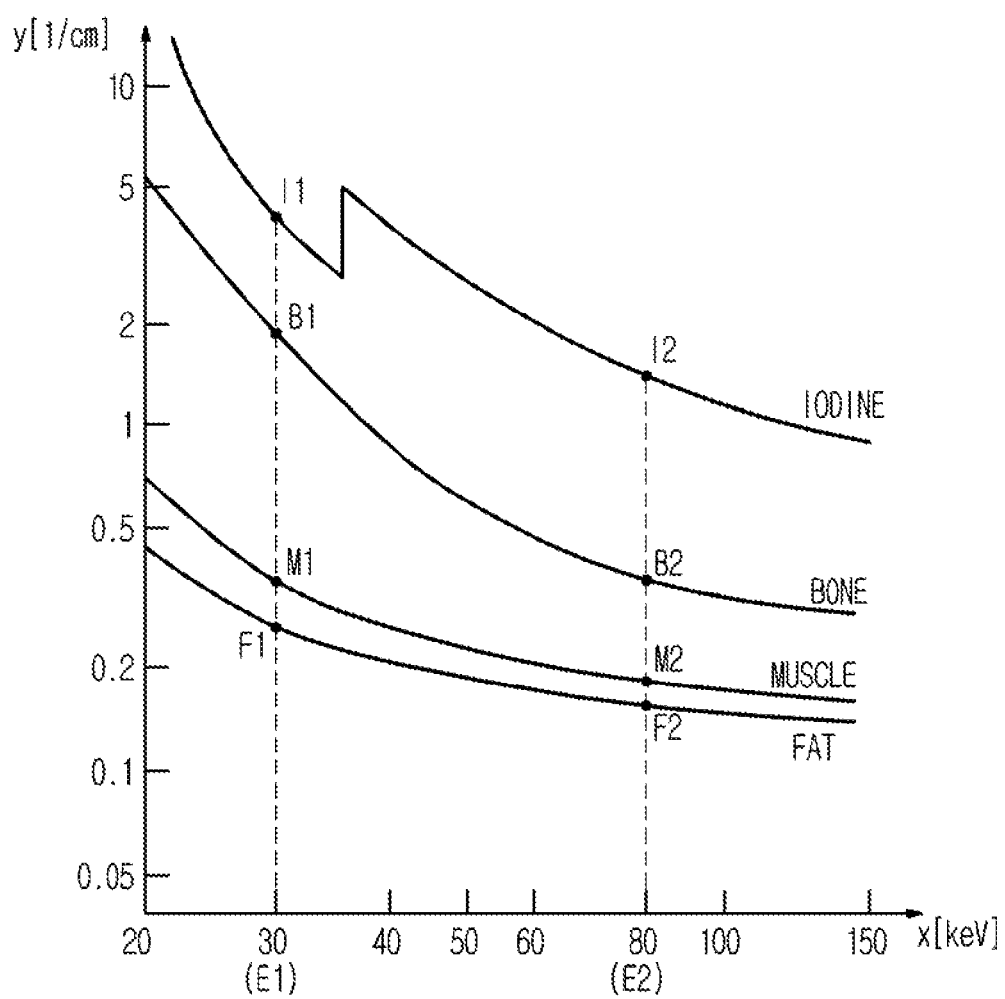
FIG. 4 is a graph showing the relationship between X-ray energy and an attenuation coefficient according to various materials inside a subject's body.

For example, a numerical expression of the degree of X-ray attenuation is referred to as an attenuation coefficient. FIG. 4 is a graph showing the relationship between X-ray energy and an attenuation coefficient according to types of tissue typically present inside a subject's body. The attenuation coefficient will now be described with reference to FIG. 4.

The attenuation coefficient may vary according to each material or tissue present inside a subject's body.

In the graph shown in FIG. 4, the x axis represents photon energy radiated onto the subject, and the y axis represents the attenuation coefficient. As shown in FIG. 4, a curve indicating an attenuation coefficient of a bone is located above a curve indicating an attenuation coefficient of a soft tissue (muscle and fat), and a curve indicating an attenuation coefficient of iodine (I) is located above the curve indicating the attenuation coefficient of the bone.

In detail, when X-rays in the same energy band, for example, E1, are radiated, an attenuation coefficient B1 of the bone is larger than an attenuation coefficient M1 of the muscle, and the attenuation coefficient M1 of the muscle is larger than an attenuation coefficient F1 of fat, and an attenuation coefficient I1 of iodine (I) is larger than the attenuation coefficient B1 of the bone.

That is, the tissues or materials inside the subject's body have different attenuation coefficients, and typically, the harder the material, the larger the attenuation coefficient of the material.

The attenuation coefficient also varies according to an energy band of the radiated X-rays.

As shown in FIG. 4, when X-rays having an energy band E1 and an energy band E2 are radiated onto bone inside the subject's body, the attenuation coefficient B1 of bone in the relatively low energy band E1 is larger than an attenuation coefficient B2 of bone in the relatively high energy band E2.

Even when the material inside the subject's body is muscle or fat, the attenuation coefficient M1 or F1, when X-rays in the relatively low energy band E1 are radiated, is larger than an attenuation coefficient M2 or F2 when X-rays in the relatively high energy band E2 are radiated. This also applies to iodine (I).

That is, the lower the energy band of the X-rays radiated onto the subject, the larger the attenuation coefficient.

The attenuation coefficient may be obtained using Equation 1 below:

$$I=I_0 \cdot e^{-\mu(E) \cdot T} \qquad \text{[Equation 1]}$$

Here, $I_0$ is the strength of X-rays radiated onto a material, I is the strength of the X-rays transmitted by the material, $\mu(E)$ is an attenuation coefficient of the material with respect to the X-rays having an energy band E, and T is a thickness of the material through which the X-rays are transmitted.

According to Equation 1, the larger the attenuation coefficient (e.g., the harder the material or the lower the energy band of the radiated X-rays) and the thicker the material, the lower the strength of the transmitted X-rays.

In order to obtain an X-ray image of a dynamic organ, such as blood vessels, a plurality imaging processes at different times is typically required. Thus, generally, the user sets an imaging period or frequency using the input unit 171 and radiates X-rays onto the subject according to the set imaging period or frequency, thereby generating an X-ray image indicating a change of the subject over time.

Accordingly, the X-rays may be radiated so as to obtain a blood vessel X-ray image according to temporal subtraction or energy subtraction. In particular, when the X-rays are radiated according to energy subtraction, energy bands of the radiated X-rays may vary. That is, when an attenuation coefficient of iodine that is a component of a contrast medium varies according to the energy band of the radiated X-rays, only an image of the blood vessels may be easily separated from the X-ray image. This will be described in more detail below.

According to at least one example embodiment, the X-ray imaging apparatus 100 illustrated in FIG. 1 may generate a moving X-ray image using fluoroscopy and may be used in the field of X-ray diagnosis, such as angiography or cardiovascular angiography, or in the field of various surgical procedures using the same. In this case, the moving X-ray image may be generated and indicated in real time.

The X-ray imaging apparatus 100 may perform X-ray imaging consecutively so as to generate the moving X-ray image. A method of consecutively performing X-ray imaging may include a consecutive exposure method and a pulse exposure method.

According to at least one example embodiment, when the consecutive exposure method is used, a low tube current is consecutively supplied to the X-ray tube 111 to generate X-rays consecutively, and when the pulse exposure method is used, X-rays are generated when a short pulse is emitted. Thus, when the pulse exposure method is used, the radiation dose of the X-rays and motion blurring can be reduced. Both methods may be applied to the X-ray imaging apparatus 100. The X-ray source 110 may be configured to radiate the X-rays onto a subject region at desired, or alternatively predetermined, or arbitrary time intervals a plurality of times. Here, the predetermined, desired, or arbitrary time intervals may be determined according to a pulse rate or a frame rate. The pulse rate may be determined according to the frame rate or vice versa. The frame rate may be set as 30 frames per second (30 fps), 15 frames per second (15 fps), and 7.5 frames per second (7.5 fps). Thus, for example, when the frame rate is set as 15 fps, the pulse rate may be set as 15 pps, and X-rays may be generated 15 times per second.

The subject is typically a subject to be imaged with X-rays, e.g., a subject, the inside of which is to be expressed as an X-ray image. The subject region is typically a region to be imaged as the X-ray image that is a desired, or alternatively predetermined region including the subject. Thus, the subject region may coincide with, or may include, an imaging region, e.g., a field of view (FOV) of the X-ray imaging apparatus 100. The collimator 112 may be disposed in the front of the X-ray source 110, e.g., in an X-ray radiation direction.

The collimator 112 may include a plurality of masks M formed of a material that absorbs or blocks the X-rays, such as, for example among others, lead or tungsten, so as to adjust an X-ray radiation region of the X-ray source 110, e.g., the range of the imaging region, e.g., the FOV, and to reduce scattering of the X-rays.

The plurality of masks M may be formed as a plurality of layers, and the masks M that constitute each of the plurality of layers may move according to a control signal and may form a region in which the X-rays are radiated, in various forms.

The X-ray detection unit 120 detects the X-rays and obtains a plurality of frame data regarding the subject region. The plurality of frame data represents each piece of a plurality of X-ray data obtained according to the frame rate of the X-ray imaging apparatus 100.

The X-ray detection unit 120 may have a two-dimensional array structure including a plurality of pixels. When the X-rays detected by the X-ray detection unit 120 are converted into electrical signals according to pixels, one piece of X-ray data regarding the subject region is generated.

In general, the X-ray detection unit 120 may be classified according to a method of converting detected X-rays into electrical signals and a method of obtaining X-ray data.

Hereinafter, various methods, whereby the X-rays are detected, the detected X-rays are converted into the electrical signals, and the X-ray data is obtained using the X-ray detection unit 120, will be described.

The X-ray detection unit 120 may be classified as a direct conversion type and an indirect conversion type according to an example method of converting the X-rays into electrical signals.

In the example direct conversion method, when the X-rays are radiated, pairs of electrons and holes are temporarily generated in a light receiving device, electrons are moved to an anode, and holes are moved to a cathode due to an electric field applied to both ends of the light receiving device. Thus, the X-ray detection unit 120 converts the movement into one or more electrical signals. In the example direct conversion method, a-Se, CdZnTe, $HgI_2$, $PbI_2$, or the like may be used as the light receiving device.

In the example indirect conversion method, a scintillator is provided between a light receiving device and an X-ray generation unit. The scintillator reacts with the X-rays radiated by the X-ray generation unit and emits photons having a wavelength in a visible light region. The light receiving device detects the photons emitted from the scintillator and converts the detected photons into electrical signals. In the example indirect conversion method, a-Si may be used as the light receiving device, and a gadolinium oxysulfide (GADOX) scintillator having a thin film shape or a micro pillar-shaped or needle-shaped CSI (TI) scintillator may be used as the scintillator.

Also, the X-ray detection unit 120 may be classified according to an example method of obtaining X-ray data into a charge integration mode where charges are stored for a desired, or alternatively predetermined amount of time, signals are obtained from the charges and a photon counting mode, where photons having an energy equal to or greater than a threshold energy are counted whenever a signal is generated from single X-ray photons.

When the X-rays are radiated by the X-ray source 110 and frame data transmitted by the subject is obtained at the frame rate set by the X-ray detection unit 120, the processor 150 may obtain an X-ray image based on the frame data transmitted from the X-ray detection unit 120. In particular, when the X-ray image of a blood vessel is obtained, the processor 150 may separate a desired internal tissue from the X-ray data, thereby obtaining only the blood vessel X-ray image.

Hereinafter, an example method of obtaining a blood vessel X-ray image, when angiography is performed using temporal subtraction or energy subtraction, will be described with reference to FIGS. 5 through 7.

Figure 5:
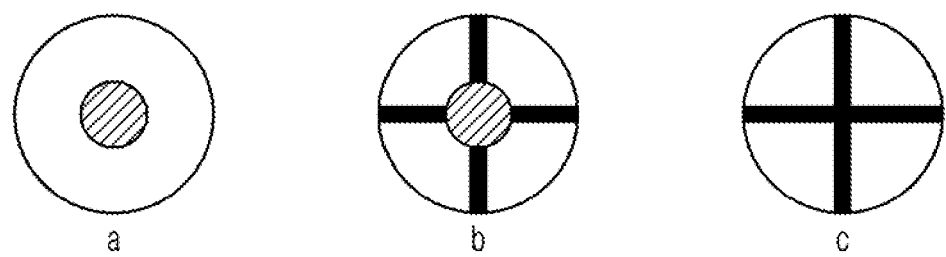
FIG. 5 schematically illustrates an X-ray image used in temporal subtraction, according to at least one example embodiment.

FIG. 5 schematically illustrates an X-ray image used in temporal subtraction. In FIG. 5, 'a' represents a mask image. The mask image is an X-ray image obtained from the subject before the contrast medium is injected into the subject. 'b' represents an X-ray image obtained from the subject after the contrast medium is injected into the subject. 'c' represents a blood vessel X-ray image that is finally obtained by temporal subtraction.

In general, blood vessels do not appear through simple X-ray imaging. However, when the contrast medium is injected into the blood vessels and X-ray imaging is performed, the shape of the blood vessels may be observed through X-ray imaging. This example method is referred to as angiography.

Figure 6A:
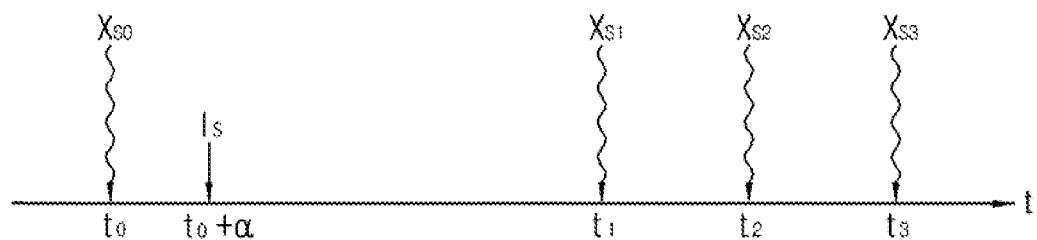
FIG. 6A illustrates a method of generating X-rays according to temporal subtraction, according to at least one example embodiment.
Figure 6B:
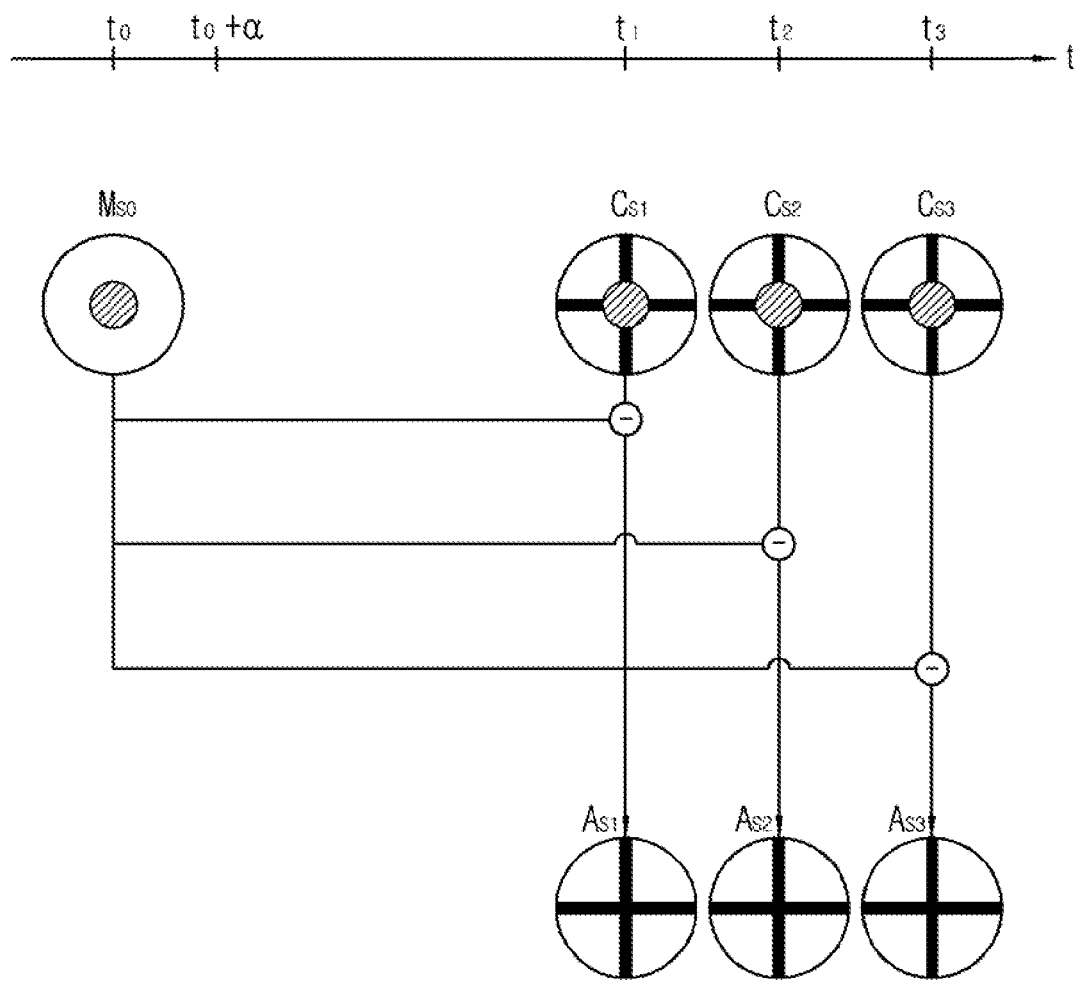
FIG. 6B illustrates a method of obtaining a blood vessel X-ray image according to temporal subtraction, according to at least one example embodiment.

Temporal subtraction is one example method of angiography. FIGS. 6A and 6B illustrate an operation of obtaining a blood vessel X-ray image according to an example temporal subtraction. When temporal subtraction is used, X-rays to be radiated may have a single energy band.

FIG. 6A illustrates an example method of generating X-rays according to temporal subtraction performed via the processor 150. $X_{S0}$, $X_{S1}$, $X_{S2}$, and $X_{S3}$ illustrate single energy X-rays, radiation times of which are $t_0$, $t_1$, $t_2$, and $t_3$. $I_S$ is a contrast medium injected into a subject at a time $(t_0+\alpha)$.

FIG. 6B illustrates an example method of obtaining a blood vessel X-ray image via the processor 150 according to temporal subtraction. $M_{S0}$ is a mask image obtained at a time $t_0$, and $C_{S1}$, $C_{S2}$, and $C_{S3}$ are single energy X-ray images obtained at times $t_1$, $t_2$, and $t_3$ after the contrast medium is injected into the subject. $A_{S1}$, $A_{S2}$, and $A_{S3}$ are blood vessel X-ray images obtained via the processor 150 according to temporal subtraction at the times $t_1$, $t_2$, and $t_3$ after the contrast medium is injected into the subject.

In order to capture a mask image that is an image before the contrast medium is injected into the subject, like in FIG. 6A, the single energy X-rays $X_{S0}$ are radiated at the time $t_0$. $M_{S0}$ that is the mask image of FIG. 6B may be obtained from the radiated X-rays $X_{S0}$.

The contrast medium $I_S$ is injected into the subject at the time $(t_0+\alpha)$ at which a desired, or alternatively predetermined amount of time elapses from the time $t_0$ at which the mask image $M_{S0}$ is obtained. In order to obtain a blood vessel image, after a sufficient time at which the contrast medium $I_S$ diffuses along the blood vessels elapses, single energy X-rays $X_{S1}$ are radiated at the desired time $t_1$.

The processor 150 may obtain the X-ray image $C_{S1}$ from the X-rays $X_{S1}$ radiated in this way after the contrast medium is injected into the subject at the time $t_1$. The processor 150 compares the X-ray image $C_{S1}$ with the mask image $M_{S0}$ after the contrast medium is injected into the subject.

Because a difference between the X-ray image $C_{S1}$ and the mask image $M_{S0}$, when there is no movement of the subject, illustrates a distribution of the contrast medium, the blood vessel X-ray image $A_{S1}$ may be obtained at the time $t_1$ by obtaining the difference, or an image of the difference, between the X-ray image $C_{S1}$ and the mask image $M_{S0}$.

When temporal subtraction is used, there is a time difference between acquisition times of a mask image and an X-ray image. As mentioned above, this time difference occurs because the X-ray image is obtained after a sufficient time for the contrast medium to diffuse to a degree into the blood vessels elapses. For example, there is a time difference between the acquisition time $t_0$ of the mask image $M_{S0}$ and the acquisition time $t_1$ of the X-ray image $C_{S1}$, as illustrated in FIGS. 6A and 6B.

The time difference may cause an error in the obtained blood vessel X-ray image. When the X-ray image is compared with the mask image after the contrast medium is injected into the subject, if a structural difference in backgrounds and contrast coincide with each other, only a blood vessel region may be comparatively precisely extracted. However, when the patient, e.g., the subject moves during diffusion of the contrast medium, a geometric deformation may occur in the X-ray image, or the movement of the subject, such as contraction or expansion, may cause an error when the blood vessel region is extracted.

Figure 7A:
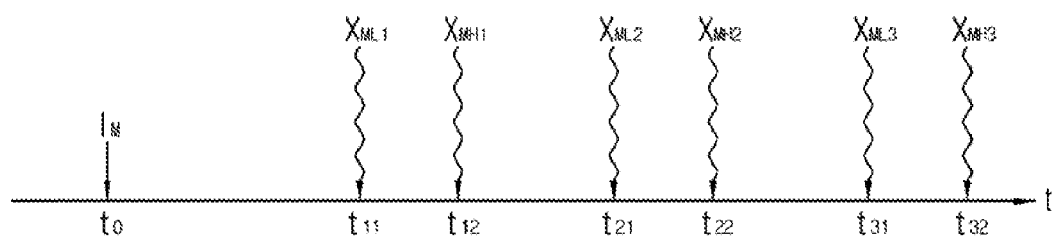
FIG. 7A illustrates a method of generating X-rays according to energy subtraction, according to at least one example embodiment.
Figure 7B:
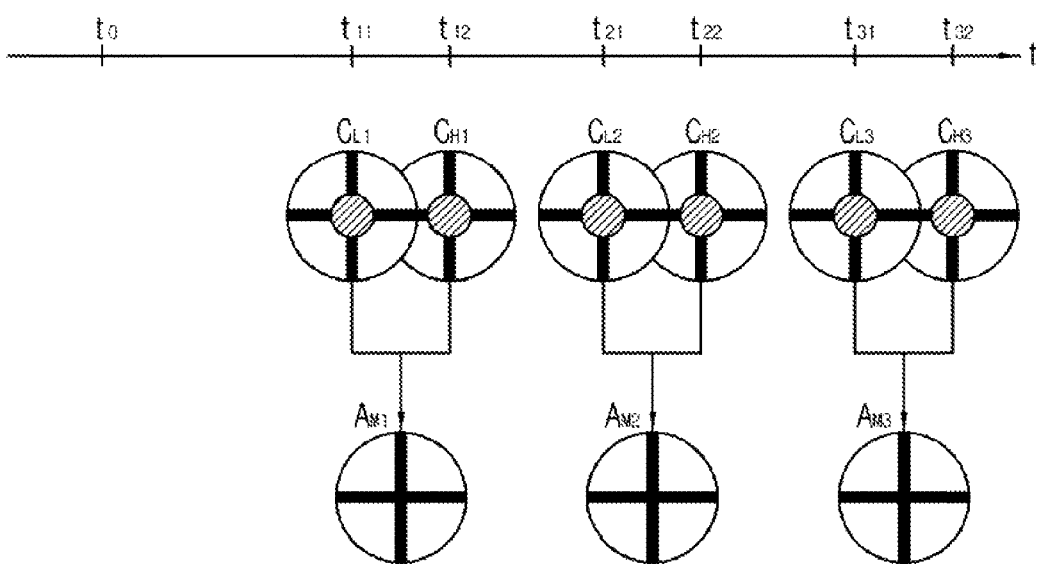
FIG. 7B illustrates a method of obtaining a blood vessel X-ray image according to energy subtraction, according to at least one example embodiment.

Angiography based on energy subtraction may be used to reduce this error. FIGS. 7A and 7B illustrate an angiography according to an example energy subtraction performed via the processor 150. In energy subtraction, X-rays having different energy bands are radiated onto the subject, unlike temporal subtraction, whereby single energy X-rays are used at different times.

FIGS. 7A and 7B illustrate an example where low energy X-rays and high energy X-rays are radiated onto the subject. Here, a high energy band and a low energy band are relative concepts and may vary.

FIG. 7A illustrates a method of generating X-rays according to energy subtraction. $X_{ML1}$, $X_{ML2}$, and $X_{ML3}$ are low energy X-rays, radiation times of which are $t_{11}$, $t_{21}$, and $t_{31}$, and $X_{MH1}$, $X_{MH2}$, and $X_{MH3}$ are high energy X-rays, radiation times of which are $t_{12}$, $t_{22}$, and $t_{32}$. $I_M$ means a contrast medium injected into the subject at a time $t_0$.

FIG. 7B illustrates an example method of obtaining a blood vessel X-ray image according to energy subtraction. $C_{L1}$, $C_{L2}$, and $C_{L3}$ are low energy X-ray images obtained at the times $t_{11}$, $t_{21}$, and $t_{31}$ after the contrast medium is injected into the subject, and $C_{H1}$, $C_{H2}$, and $C_{H3}$ are high energy X-ray images obtained at the times $t_{12}$, $t_{22}$, and $t_{32}$ after the contrast medium is injected into the subject. $A_{M1}$, $A_{M2}$, and $A_{M3}$ are blood vessel X-ray images obtained using energy subtraction at times $t_1$, $t_2$, and $t_3$ after the contrast medium is injected into the subject.

As shown in FIG. 7A, the contrast medium $I_M$ is injected into the subject before the X-rays are radiated. A sufficient time at which the contrast medium $I_M$ diffuses along blood vessels, is advantageous in obtaining a blood vessel image.

The X-ray source 110 radiates X-rays so as to obtain X-ray images corresponding to two different energy bands. To this end, the X-ray source 110 may radiate X-rays having a high energy band and X-rays having a low energy band, or the X-ray source 110 may radiate wide-band X-rays including two energy bands once, and the X-ray detection unit 120 may separate the detected X-rays into X-rays having a high energy band and X-rays having a low energy band.

An example embodiment of the X-ray imaging apparatus 100 and the method of controlling the same in which the X-ray detection unit 120 sequentially radiates X-rays having a high energy band and X-rays having a low energy band, will now be described. Referring to FIG. 7A, the low energy X-rays $X_{ML1}$ and the high energy X-rays $X_{MH1}$ are radiated at times $t_{11}$ and $t_{12}$ after a sufficient time for the contrast medium $I_M$ to diffuse into the blood vessels elapses.

When two types of materials are separated in an X-ray image, materials to be separated may have different X-ray attenuation characteristics, and X-ray images corresponding to different energy bands may have to be obtained.

To this end, the processor 150 may generate X-ray images corresponding to different energy bands. For example, as illustrated in FIG. 7B, corresponding to the low energy X-rays $X_{ML1}$ and the high energy X-rays $X_{MH1}$, the processor 150 may generate a low energy X-ray image $C_{L1}$ and a high energy X-ray image $C_{H1}$ sequentially, or in reverse order, after the contrast medium $I_M$ is injected into the subject.

In the X-ray images $C_{L1}$ and $C_{H1}$ thus generated, there is a difference in brightness between the blood vessels (contrast medium), the bones, and the calcification tissues that are materials to be separated inside the subject. This is because, as described above, attenuation characteristics of the materials are different depending on energy bands of X-rays.

According to at least one example embodiment, the processor 150 separates a blood vessel image from an original image. The processor 150 may separate two material images by performing an arithmetic operation of multiplying at least one of the two X-ray images $C_{L1}$ and $C_{H1}$ by a desired, or alternatively predetermined weighted value, and subtracting the desired weighted value from the other of the two X-ray images twice. This is referred to as dual-energy X-ray absorptiometry. For example, the blood vessel X-ray image may be obtained by multiplying the low energy X-ray image $C_{L1}$ by the desired, or alternatively predetermined weighted value and subtracting the weighted value from the high energy X-ray image $C_{H1}$, so as to separate blood vessels from the bones and the calcification tissues. That is, an image in which the bones and a lime material are removed and blood vessels clearly appear, can be obtained.

Alternatively, when materials to be separated are three or more types including blood vessels, the processor 150 may generate three or more X-ray images corresponding to three or more energy bands, multiply each of the X-ray images by an appropriate or alternatively desired weighted value, subtract the weighted value from the other X-ray image, thereby separating three or more types of material images including blood vessels.

As described above, the X-ray imaging apparatus 100 does not limit the number of materials to be separated, may obtain an original image according to the number of materials to be separated, and may separate each material image using attenuation characteristics according to each one of the materials.

Also, a method of separating material images by multiplying a material image by a weighted value and subtracting the weighted value from the other material image is one method used in the processor 150, and other methods may also be used in material image separation.

In this way, the processor 150 may generate the blood vessel X-ray image $A_{M1}$ using the X-ray images $C_{L1}$ and $C_{H1}$. As a result of sequentially radiating low energy X-rays and high energy X-rays, one blood vessel X-ray image corresponding to the low energy X-rays and the high energy X-rays may be obtained.

In an example angiography according to energy subtraction, a difference between acquisition times of a low energy image and a high energy image that are used as a basis for the obtained blood vessel X-ray images may be smaller than a time difference between an acquisition time of a mask image using temporal subtraction and an acquisition time of an X-ray image after the contrast medium is injected into the subject. In temporal subtraction, the X-rays cannot be radiated onto the subject while the contrast medium diffuses into the blood vessels, but in energy subtraction, the X-rays of multiple energy levels can be sequentially radiated onto the subject even when the contrast medium did not entirely diffuse into the blood vessels.

Thus, a period of time during which movement of the subject may occur when energy subtraction is used is shorter than the period of time during which movement of the subject may occur when temporal subtraction is used. As a result, an error that may occur due to movement of the subject during a difference between acquisition times of two images when energy subtraction is used, may be less than an error that may occur due to movement of the subject during the difference between the acquisition times of two images when temporal subtraction is used.

However, a blood vessel X-ray image obtained using energy subtraction typically has a lower signal to noise ratio (SNR) than an SNR of a blood vessel X-ray image obtained using temporal subtraction.

Since the larger the SNR, the clearer the quality of an obtained image, a clear X-ray image in which less noise is included may be obtained when temporal subtraction is used.

Accordingly, in temporal subtraction, there is a high possibility of error occurrence due to movement of the subject in spite of a high SNR, whereas, in energy subtraction, a lower SNR than in temporal subtraction is achieved but an error caused by movement of the subject can be reduced.

According to at least one example embodiment, the controller 160 may set parameters relating to injection of the contrast medium and imaging parameters for controlling the X-ray source 110, the collimator 112, and the X-ray detection unit 120 in regard to X-ray imaging so that injection of the contrast medium or X-ray imaging can be performed in a substantially optimum condition.

The parameters relating to injection of the contrast medium may include the injection amount of the contrast medium, an injection time, and a concentration of the contrast medium. The imaging parameters are also referred to as exposure parameters, and automatically controlling the imaging parameters using the X-ray imaging apparatus 100 is referred to as auto exposure control, automatic brightness control, automatic dose control, or automatic dose rate control.

According to at least one example embodiment, the imaging parameters may include a tube voltage, a tube current, an exposure time, the type of a filter, an imaging region, e.g., an FOV, a frame rate, a pulse rate, and the type of a target material.

The imaging parameters may be determined based on a frame image regarding the subject region obtained by the processor 150 or based on previous information input before X-ray imaging starts. Hereinafter, an example embodiment regarding the former case will be described in detail.

The controller 160 may determine imaging parameters based on an analysis result of the processor 150. For example, if the processor 150 determines characteristics, such as a thickness or density of the subject, by analyzing a frame image, the controller 160 may determine imaging parameters, such as a tube voltage, a tube current, an exposure time, the type of a filter, and the type of a target material, that may be suitable for characteristics of the subject, based on the determination result.

Also, the controller 160 may determine imaging parameters based on information regarding a region of interest (ROI) obtained by the processor 150. In an example embodiment, the controller 160 may determine imaging parameters, such as a frame rate, a tube current, and a dose per frame, according to, for example, the size of movement of an object of interest, or characteristics of an image that appears in the ROI, thereby individually or simultaneously controlling the imaging parameters.

For example, the controller 160 may obtain information regarding movement of the object of interest as much as possible by increasing the frame rate when the size of movement of the object of interest is relatively large, and the controller 160 may reduce X-ray radiation exposure of the subject by reducing the frame rate when the size of movement of the object of interest is relatively small.

Also, the controller 160 may control the dose per frame according to a noise level of the ROI. For example, if the noise level of the ROI is higher than a desired, or alternatively predetermined reference value, the dose per frame is increased to reduce the noise level so that the ROI can appear clearer, and if the noise level of the ROI is lower than the desired, or alternatively predetermined reference value, the dose per frame is decreased so that the amount of X-ray radiation exposure of the subject can be reduced.

Also, whether the ROI among regions of the subject is set by the processor 150 or by an operating person, the controller 160 may adjust the collimator 112 so that the X-rays may be radiated onto only the ROI and an imaging region may be limited to the ROI. If the imaging region is limited to the ROI, the X-rays radiated onto the subject may be reduced so that the amount of X-ray radiation exposure of the subject can be reduced. In the example embodiment, a method is described, whereby the object of interest, e.g., a surgical instrument such as a catheter, of the ROI is traced using a tracing filter such as an extended Kalman filter so as to reduce the amount of X-ray radiation exposure of the subject, and the tracing result of the object of interest is correlated with the collimator so that an X-ray radiation region can be adjusted, for example automatically adjusted, is suggested. Typically, a Kalman filter, also known as linear quadratic estimation (LQE), is an algorithm that uses a series of measurements observed over time, containing noise or other random variations and inaccuracies and produces estimates of unknown variables that tend to be more precise than those based on a single measurement alone. Hereinafter, this will be method is described in detail.

Figure 8:
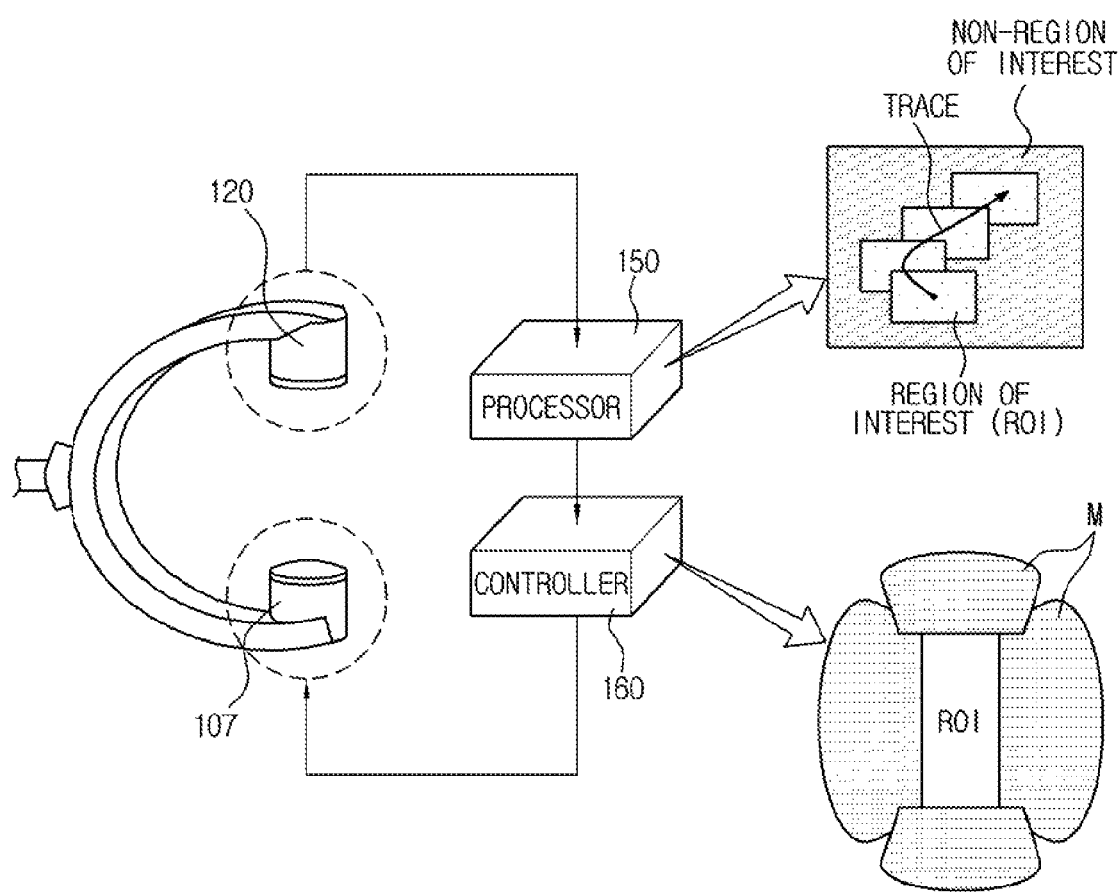
FIG. 8 is a conceptual view illustrating an operation of tracking an object of interest and controlling driving of a collimator so as to interlock an X-ray radiation region with tracing the object using the example X-ray imaging apparatus of FIG. 1.
Figure 9:
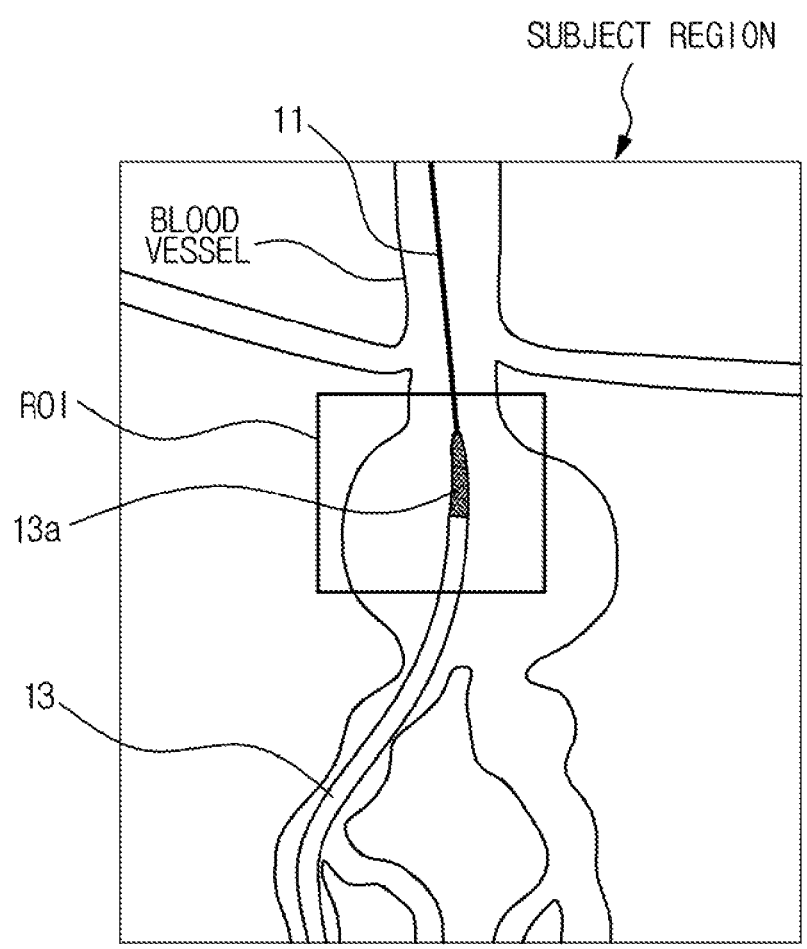
FIG. 9 illustrates a region of interest (ROI) in case of endovascular stent grafting, according to at least one example embodiment.
Figure 10:
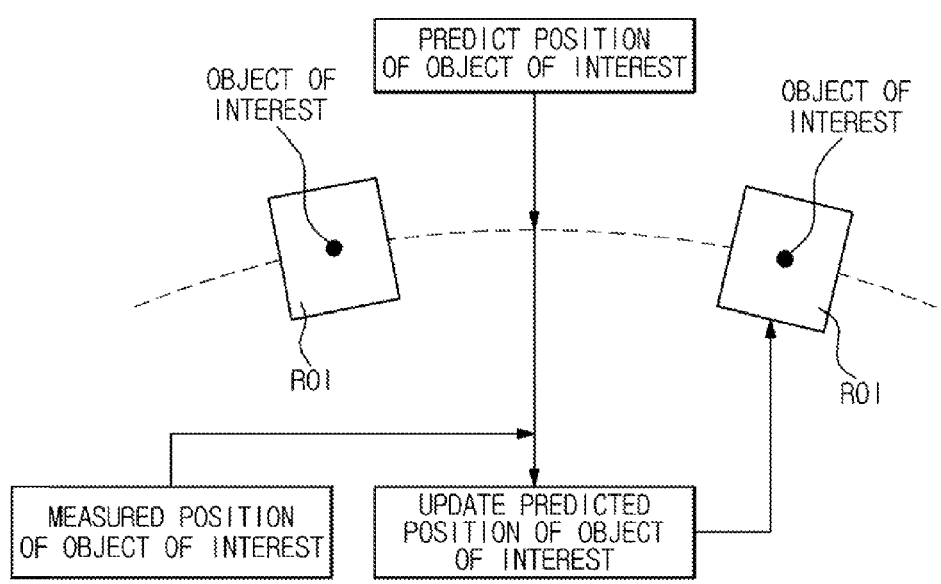
FIG. 10 is a conceptual view illustrating an operation of tracing the object of interest using an extended Kalman filter, according to at least one example embodiment.
Figure 11:
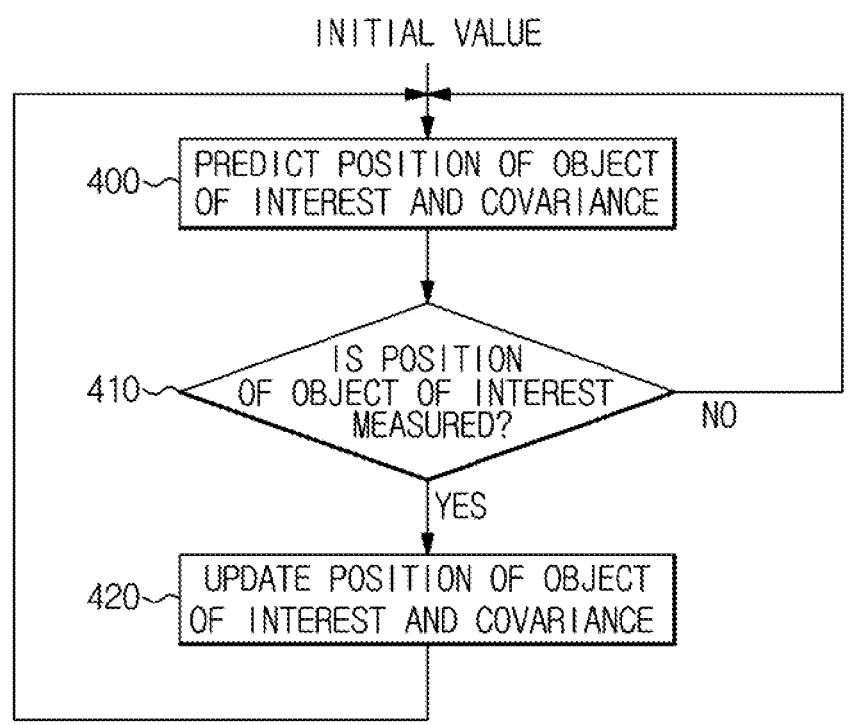
FIG. 11 is a flow chart illustrating an X-ray imaging method of tracing an object of interest, according to at least one example embodiment.
Figure 12:
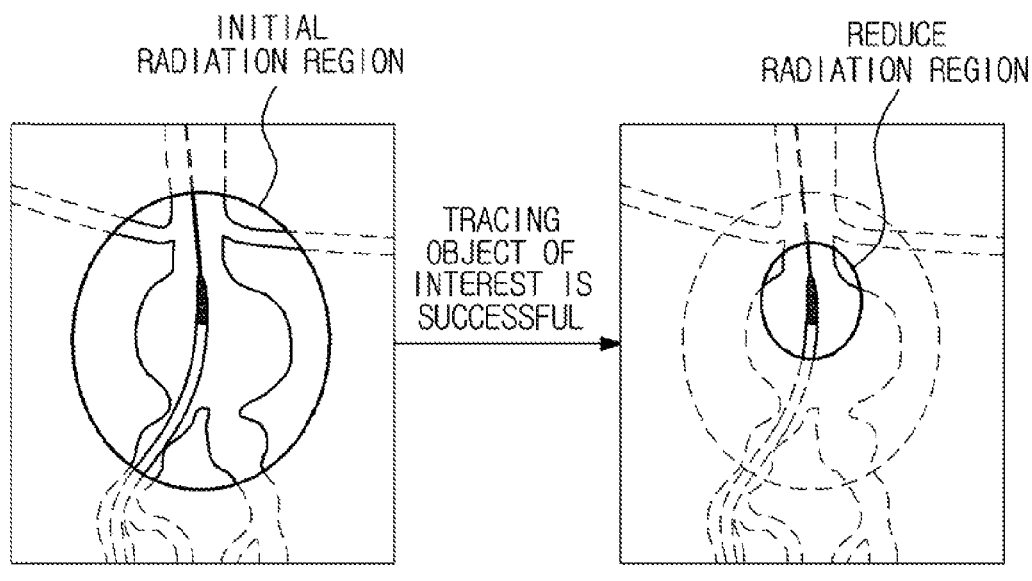
FIG. 12 illustrates a case where the X-ray radiation region varies while interlocking with tracing the object of interest, according to at least one example embodiment.
Figure 12:
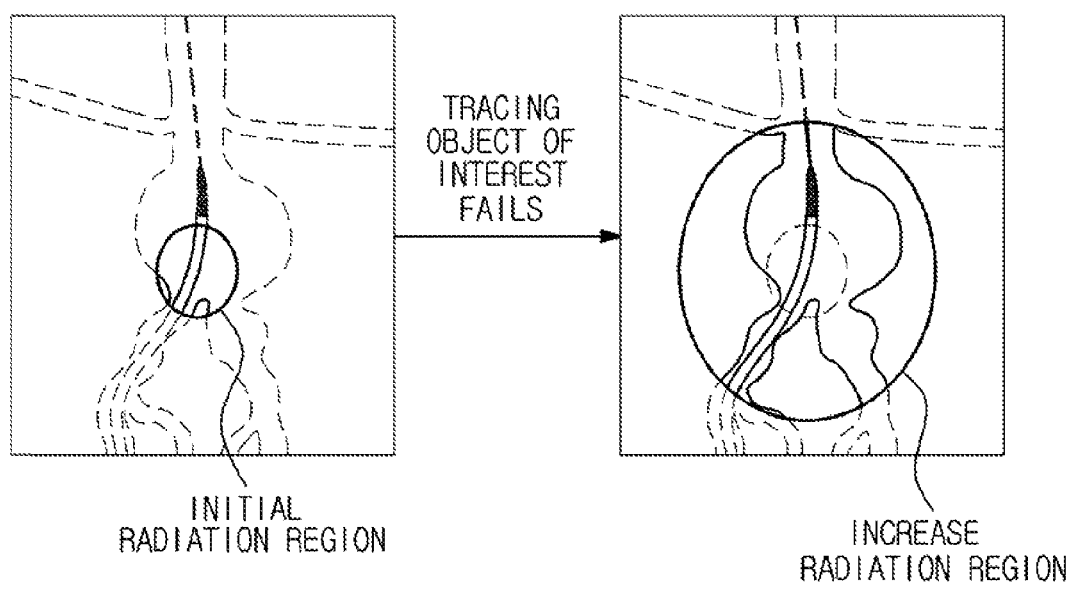
Figure 13:
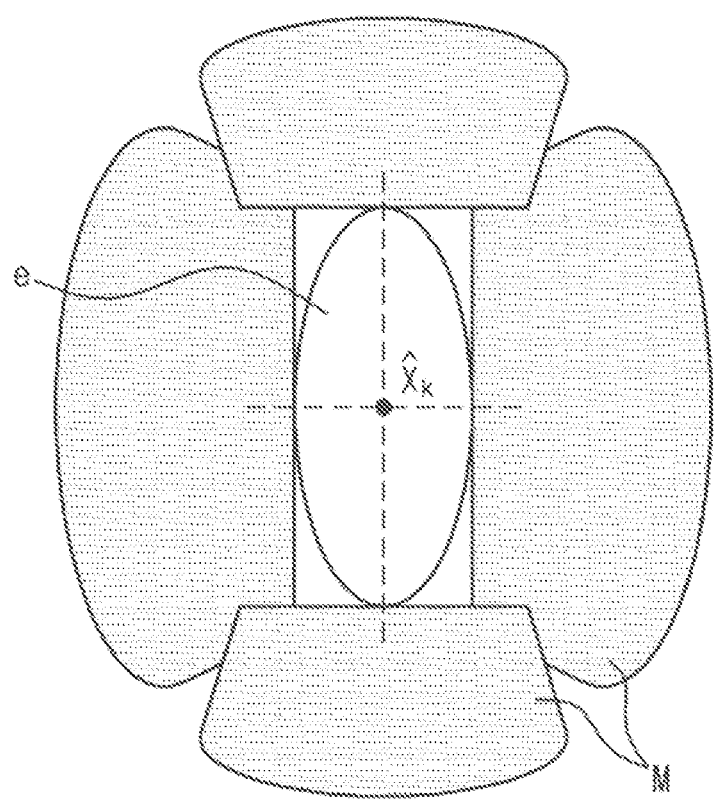
FIG. 13 illustrates a case where a mask of the collimator adjusts the X-ray radiation region according to an oval formed due to the result of tracing, according to at least one example embodiment.

FIG. 8 is a conceptual view illustrating an example operation of controlling driving of the collimator 112 so as to trace the object of interest and to correlate the X-ray radiation region with the tracing result using the X-ray imaging apparatus 100 of FIG. 1. FIG. 9 illustrates the ROI in case of endovascular stent grafting. FIGS. 10 and 11 are conceptual views illustrating an example operation of tracing the object of interest using the extended Kalman filter. FIG. 12 illustrates an example where the X-ray radiation region varies while being correlated with the tracing result of the object of interest, and FIG. 13 illustrates an example where the mask M of the collimator 112 adjusts the X-ray radiation region corresponding to an oval formed due to the tracing result.

According to at least one example embodiment, the processor 150 obtains the X-ray image based on the data obtained by the X-ray detection unit 120, and sets the ROI in the X-ray image. The processor 150 determines the ROI in the frame image regarding the subject region. The ROI is typically a region of the subject region in which the object of interest is tracked. In order to determine the ROI, the processor 150 detects the object of interest. In order to detect the object of interest, the processor 150 may previously store features of the object of interest and may detect the object corresponding to the previously-stored features from the frame image regarding the subject region. For example, features of the object of interest that may be detected from the X-ray image, such as a shape of the object of interest, X-ray absorption characteristics, and movement characteristics, may be previously stored. Here, the movement characteristics of the object of interest may include information regarding movement of the object of interest, and the information regarding the movement of the object of interest may include a movement direction, a movement speed, and a position change.

The object of interest that is an object to be continuously observed by the user during X-ray imaging, may be a surgical instrument used in the subject, or a part on which a surgical procedure is to be performed. For example, when the X-ray imaging apparatus 100 is used in an angiography, detailed observation of surgical instruments is required when the surgical instruments, such as a guide wire, a catheter, a needle, a balloon, and/or a stent, are inserted into the blood vessels. Thus, the surgical instruments may be set as the object of interest, and information regarding features of the surgical instruments may be previously stored.

Also, when the surgical part is set as the object of interest, stenosis, aneurysm, and a lesion region, such as a cancerous region, may be the object of interest.

If the object of interest is detected, the processor 150 may set a desired, or alternatively predetermined region including the detected object of interest as the ROI. Thus, the position and size of the ROI may be determined in consideration of the position, size, and movement characteristics of the object of interest.

FIG. 9 illustrates the ROI in case of endovascular stent grafting, according to at least one example embodiment. Referring to the example illustrated in FIG. 9, a stent 13a is inserted into the blood vessels so as to reduce or prevent blockage of the blood vessels, and has a mesh shape. The stent 13a is mounted at an end of a stent instrument 13 having the shape of a tube in a folded state, is injected into the blood vessels, and is unfolded in mesh form.

In order to insert the stent instrument 13 into the blood vessels of the subject region, a guide wire 11 is inserted. The stent instrument 13 is inserted into the blood vessels along the guide wire 11, and while the stent instrument 13 is inserted into the blood vessels, the stent instrument 13, and in particular the stent 13a at an end of the stent instrument 13, may be the object of interest, and the desired, or alternatively predetermined region including the stent 13a may be the ROI.

While the guide wire 11 is inserted, the guide wire 11 or a tip of the guide wire 11 may be the object of interest, and although not shown, while the catheter is inserted so as to inject the contrast medium into the blood vessels, the catheter or a tip of the catheter may be the object of interest.

According to at least one example embodiment, the processor 150 may use information input from the outside so as to detect the object of interest. For example, if information regarding the type of a surgical instrument, the type of a surgical procedure, and a surgical part and information regarding whether the contrast medium is injected, are input in the processor 150, the object of interest may be detected from the frame image based on the input information. Alternatively, the ROI may be selected and determined by an operating person.

When the ROI is determined, the processor 150 traces the object of interest. Here, the object of interest may be set as the surgical instrument, for example, the tip of the catheter. The processor 150 may use the extended Kalman filter as a tracing filter so as to trace the position of the object of interest.

Referring to FIG. 10, the extended Kalman filter is used to calculate, via the processor 150, a prediction value of the position of the object of interest, and a prediction value of the error covariance indicative of a probability that the object of interest will exist in a predicted position (400), and may be used to update, via the processor 150, the prediction value of the position of the object of interest and the prediction value of the error covariance using a measurement value of the position of the object of interest detected from the X-ray image (420), thereby calculating via the processor 150 an estimated value of the position of the object of interest and an estimated value of the error covariance and tracing the position of the object of interest. The following equation represents a prediction procedure and an updating procedure of the extended Kalman filter.

<Prediction>

$$\hat{X}^-_k = F\hat{X}_{k-1} \qquad \text{<Equation 1>}$$

$$\hat{P}^-_k = F\hat{P}_{k-1}F^T + Q \qquad \text{<Equation 2>}$$

<Update>

$$K_k = \hat{P}^-_k H^T (H\hat{P}^-_k H^T + R) \qquad \text{<Equation 3>}$$

$$\hat{X}_k = \hat{X}^-_k + K_k(Y_k - H\hat{X}^-_k) \qquad \text{<Equation 4>}$$

$$\hat{P}_k = (I - K_k H)\hat{P}^-_k \qquad \text{<Equation 5>}$$

Prediction of an estimated value of a state of the object of interest is shown in Equation 1. $X_k$ is a variable indicative of the state of the object of interest to be traced, and $\hat{X}_k$ is an estimated value of the state of the object of interest, and $\hat{X}^-_k$ is a prediction value of the estimated value of the state of the object of interest. The variable indicative of the state of the object of interest may include position and speed of the object of interest.

Prediction of an estimated value of the error covariance, which is indicative of accuracy of the prediction value shown in Equation 1, is shown in Equation 2. Q is the process covariance, $\hat{P}_k$ is an estimated value of the error covariance, and $\hat{P}^-_k$ is a prediction value of the estimated value of the error covariance. F is a matrix obtained by modeling of a system.

Through the prediction procedures shown in Equations 1 and 2, the processor 150 is capable of predicting, and predicts, an estimated value of the position of the object of interest and is capable of predicting, and predicts, an estimated value of the error covariance indicative of a probability that the object of interest will exist in the predicted position.

Referring to Equations 3 through 5, the extended Kalman filter updates the prediction value of the estimated value of the position of the object of interest obtained and the prediction value of the estimated value of the error covariance obtained in the prediction procedure using the measurement value of the position of the object of interest, thereby obtaining an estimated value of the position of the object of interest and an estimated value of the error covariance. The extended Kalman filter calculates a Kalman gain in this procedure and uses the Kalman gain as a weighted value of a difference between the measurement value and the prediction value.

In Equation 3, $K_k$ is a Kalman gain, and R is measurement covariance. In Equation 4, $Y_k$ is a measurement value of the position of the object of interest detected from the X-ray image. A prediction value ($\hat{X}^-_k$, $\hat{P}^-_k$) obtained in the prediction procedure is updated using the measurement value and measurement covariance ($Y_k$, R) so that an estimated value ($\hat{X}_k$) of the position of the object of interest and an estimated value ($\hat{P}_k$) of the error covariance indicative of a probability that the object of interest will exist in the estimated position are obtained.

According to at least one example embodiment, the extended Kalman filter performs the prediction and updating procedures repeatedly, thereby tracing the position of the object of interest, as illustrated in FIG. 11, which is a flow chart illustrating an X-ray imaging method of tracing an object of interest, according to at least one example embodiment. If the object of interest stops or moves along a clear movement path and tracing the object of interest is well performed (move to "YES" in Operation 410), a value of error covariance decreases through the prediction and updating procedures. In this case, even when X-rays are radiated only in a small region including the object of interest, tracing the object of interest can be performed. However, when the object of interest moves suddenly, or when the position of the object of interest is unclear due to injection of the contrast medium, the object of interest may not be readily detected from the X-ray image, and only the prediction procedure is repeatedly performed without performing the updating procedure (move to "NO" in Operation 410). Thus, the error covariance increases gradually. In this case, a region in which the X-rays are radiated needs to be extended so that the object of interest can be detected.

When the X-ray radiation region is adjusted according to a change in covariance by correlating the error covariance with the X-ray radiation region adjusted by the collimator 112, if tracking the object of interest is well performed, the error covariance decreases, and the X-ray radiation region is reduced as a result. If tracing the object of interest is not well performed, for example when missing the object of interest, the error covariance increases, and the X-ray radiation region increases as a result.

Accordingly, if the collimator 112 is controlled so that the X-ray radiation region may be correlated with the covariance, as illustrated in FIG. 12, when tracking the object of interest, for example tracking the catheter, is normally performed, the X-rays are radiated mostly or only in a narrow region including the catheter so that the amount of X-ray radiation exposure of the subject can be reduced. When the catheter is not tracked or located due to a rapid movement of the catheter or due to shielding, the updating procedure is not performed, and only the prediction procedure is performed by the extended Kalman filter, and the X-ray radiation region is extended or broadened, as illustrated in FIG. 12, so as to track the catheter. That is, in a situation where the catheter makes a rapid movement, the X-rays are radiated in a wide region, and in a situation where movement of the catheter stops or slows down, the X-rays are radiated onto a narrow region so that the amount of X-ray radiation exposure can be reduced.

Accordingly, if the X-ray radiation region is correlated with the change in error covariance, a workflow of the operating person is not disturbed, and the object of interest can be efficiently tracked and the amount of X-ray radiation exposure of the subject can also be reduced, for example contemporaneously or simultaneously.

In order for the X-ray radiation region to be correlated with the change of error covariance, the processor 150 may set the following Equation 6 using the estimated value of the position of the object of interest and the estimated value of the error covariance that are output values of the extended Kalman filter. According to the following Equation 6, an oval having a center of $\hat{X}_k$ is formed.

$$(X-\hat{X}_k)^T \hat{P}_k (X-\hat{X}_k) = 1. \qquad \text{<Equation 6>}$$

The processor 150 controls the mask M of the collimator 112 in such a way that the X-ray radiation region may be formed as a rectangle including sides having lengths corresponding to a long axis and a short axis of the oval, so that the X-ray radiation region can be correlated with the change in covariance of the extended Kalman filter, as illustrated in FIG. 13. If the processor 150 outputs signals for controlling the collimator 112, the controller 160 drives the mask M of the collimator 112 according to the signals.

As described above, since the position of the object of interest and the movement speed of the object of interest are included in the variable indicative of the state of the object of interest to be traced, a speed estimated value as well as the position of the object of interest can be obtained. Thus, if the object of interest moves at a desired, or alternatively predetermined speed and a proceeding direction is determined, covariance with respect to the proceeding direction of the object of interest increases, and the long axis of the oval formed according to Equation 6 increases in the proceeding direction.

Figure 14:
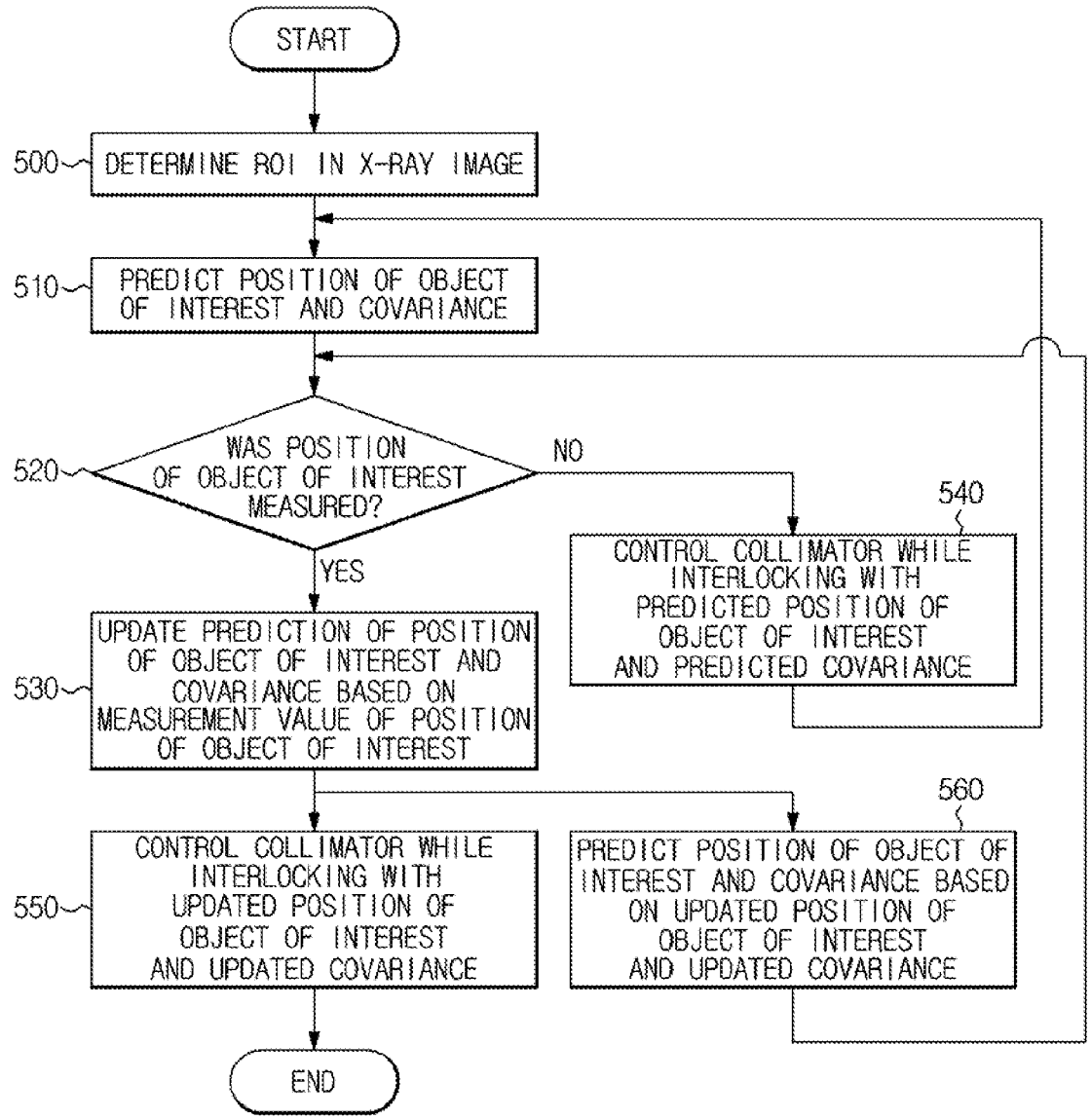
FIG. 14 is a flowchart illustrating a method of controlling the X-ray imaging apparatus of FIG. 1, in accordance with at least one example embodiment.

FIG. 14 is a flowchart illustrating an example method of controlling the X-ray imaging apparatus of FIG. 1, in accordance with an example embodiment.

Referring to FIG. 14, the processor 150 determines a region of interest (ROI) in an X-ray image (500) and predicts a position of an object of interest that exists in the ROI and covariance (510). If the position of the object of interest is measured in the X-ray image (520), prediction of the position of the object of interest and covariance are updated via the processor 150 based on a measurement value of the position of the object of interest (530). If the position of the object of interest and covariance are updated, the position of the object of interest and covariance are predicted via the processor 150 based on the updated position of the object of interest and covariance (560), thereby repeatedly performing the prediction and updating procedures.

According to at least one example embodiment, the processor 150 obtains an X-ray image based on data obtained by the X-ray detection unit 120 and sets the ROI in the X-ray image. The processor 150 determines the ROI in a frame image of a subject region. The ROI means a region of the subject region in which the object of interest exists. In order to determine the ROI, the processor 150 detects the object of interest. The object of interest that is an object to be continuously observed by the user during X-ray imaging, may be a surgical instrument used in the subject or a part on which a surgical procedure is to be performed. For example, when the X-ray imaging apparatus 100 is used in an angiography, detailed observation of surgical instruments is required when the surgical instruments, such as a guide wire, a catheter, a needle, a balloon, and/or a stent, are inserted into the blood vessels. Thus, the surgical instruments may be set as the object of interest, and information regarding features of the surgical instruments may be previously stored. Also, when the surgical part is set as the object of interest, stenosis, aneurysm, and a lesion region, such as a cancerous region, may be the object of interest.

If the object of interest is detected, the processor 150 sets a desired, or alternatively predetermined region including the detected object of interest as the ROI. Thus, the position and size of the ROI may be determined in consideration of the position, size, and movement characteristics of the object of interest.

The processor 150 may use information input from the outside so as to detect the object of interest. For example, if information regarding the type of surgical instrument, the type of surgical procedure, and surgical part and information regarding whether the contrast medium is injected, are input, the object of interest may be detected from the frame image based on the input information. Also, the ROI may be selected and determined by an operating person.

If the ROI is determined in the above-discussed manner, the processor 150 traces the object of interest. Here, the object of interest may be set as the surgical instrument, for example, the tip of the catheter. The processor 150 may use the extended Kalman filter as a tracing filter so as to trace the position of the object of interest.

The extended Kalman filter may be used to calculate, via the processor 150, a prediction value of the position of the object of interest and a prediction value of the error covariance indicative of a probability that the object of interest will exist in a predicted position, and may be used to update, via the processor 150, the prediction value of the estimated value of the position of the object of interest and the prediction value of the estimated value of error covariance using a measurement value of the position of the object of interest detected from the X-ray image, thereby calculating an estimated value of the position of the object of interest and an estimated value of the error covariance, and tracking the position of the object of interest.

If the position of the object of interest is not measured in the X-ray image (520), the collimator 112 is controlled so that the X-ray radiation region may be correlated with the predicted position of the object of interest and covariance (540), and if the position of the object of interest and covariance are updated, the collimator 112 is controlled so that the X-ray radiation region may be correlated with the updated position of the object of interest and covariance (550).

The extended Kalman filter repeatedly performs the prediction and updating procedures, thereby tracking the position of the object of interest, as illustrated in FIG. 11. If the object of interest stops or moves along a clear movement path and tracking the object of interest is well performed (move to "YES" in Operation 520), a value of the error covariance decreases through the prediction and updating procedures. In this case, even when X-rays are radiated only in a small region including the object of interest, tracking the object of interest can be performed. However, when the object of interest moves suddenly, or when the position of the object of interest is unclear due to injection of the contrast medium, the object of interest cannot be detected from the X-ray image, and only the prediction procedure is repeatedly performed without performing the updating procedure (move to "NO" in Operation 520). Thus, the error covariance increases gradually. In this case, a region in which the X-rays are radiated needs to be extended or broadened so that the object of interest can be detected.

When the X-ray radiation region is adjusted according to a change in covariance by correlating the error covariance with the X-ray radiation region adjusted by the collimator 112, if tracking the object of interest is well performed, the error covariance decreases and thus, the X-ray radiation region is reduced. If tracing the object of interest is not well performed, like missing the object of interest, the error covariance increases and thus, the X-ray radiation region increases, for example automatically.

Thus, if the collimator 112 is controlled so that the X-ray radiation region may be correlated with covariance, as illustrated in FIG. 12, when tracing the object of interest, for example, tracing the catheter, is normally performed, the X-rays are radiated mostly or only in a narrow region including the catheter so that the amount of X-ray radiation exposure of the subject can be reduced. When the catheter is not traced due to rapid movement or shielding, the updating procedure is not performed, and only the prediction procedure is performed by the extended Kalman filter, and the X-ray radiation region is extended, as illustrated in FIG. 12. That is, in a situation where the catheter makes a rapid movement, the X-rays are radiated in a wide region, and in a situation where movement of the catheter stops or slows down, the X-rays may be radiated onto a narrow region so that the amount of X-ray radiation exposure can be reduced.

Accordingly, if the X-ray radiation region is correlated with the change in error covariance, the workflow of the operating person is not disturbed, and the object of interest can be efficiently traced, and the amount of X-ray radiation exposure of the subject can also be reduced.

As described above, in accordance with at least one example embodiment, the radiation dose of X-rays radiated onto the subject can be reduced.

Also, the operating person can concentrate on a surgical procedure without taking an additional action so as to reduce the radiation dose of the X-rays.

The X-Ray imaging apparatus may include the processor 150 and a memory (not shown).

The processor 150 may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform the operations illustrated in FIGS. 11 and 14 such that the processor generates a plurality of encoded pulse signals based on an external master clock signal.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion.

Although a few example embodiments have been shown and described, it would be appreciated by those skilled in the art that changes may be made in these example embodiments without departing from the principles and spirit of the embodiments, the scope of which is defined in the claims and their equivalents.

What is claimed is:

1. An X-ray imaging apparatus comprising:
   an X-ray source;
   a single collimator configured to adjust a radiation region of X-rays radiated by the X-ray source;

a processor configured to determine a region of interest (ROI) in an X-ray image, to track a position of an object of interest in the ROI; and a controller configured to control the single collimator so that a region in which the X-rays are radiated is correlated with a result of tracking the object of interest, wherein the processor is configured to predict the position of the object of interest, to predict covariance indicative of accuracy of the prediction, and to update the prediction of the position of the object of interest and the covariance based on a measurement value of the position of the object of interest in the X-ray image.

2. The X-ray imaging apparatus of claim 1, wherein the controller is configured to control the single collimator so that a position and an area of the region in which the X-rays are radiated are determined in correlation with the updated position of the object of interest and the updated covariance.

3. The X-ray imaging apparatus of claim 1, wherein the processor is configured to set an oval region in which the position of the object of interest is included based on the updated position of the object of interest and the updated covariance, and the controller is configured to control the single collimator so that the area of the X-ray radiation region corresponds to an area of the region.

4. The X-ray imaging apparatus of claim 1, wherein, if the position of the object of interest is not measured in the X-ray image, the processor is configured to repeatedly perform a procedure of predicting the position of the object of interest and covariance based on the predicted position of the object of interest and the predicted covariance.

5. The X-ray imaging apparatus of claim 4, wherein the controller is configured to control the single collimator so that the position and the area of the region in which the X-rays are radiated are determined in correlation with the predicted position of the object of interest and the predicted covariance.

6. The X-ray imaging apparatus of claim 4, wherein the processor is configured to set an oval region in which the position of the object of interest is included based on the predicted position of the object of interest and the predicted covariance, and to control the single collimator so that the area of the X-ray radiation region corresponds to an area of the oval region.

7. The X-ray imaging apparatus of claim 1, wherein the processor is configured to track the position and speed of the object of interest in the ROI.

8. A method of controlling an X-ray imaging apparatus, the method comprising:

determining, via a processor, a region of interest (ROI) in an X-ray image;

tracking, via the processor, a position of an object of interest in the ROI; and controlling, via a controller, a single collimator so that a region in which X-rays are radiated is correlated with a result of tracking the object of interest, wherein the tracking of the position of the object of interest includes:

predicting the position of the object of interest and predicting a covariance indicative of accuracy of the prediction;

updating the prediction of the position of the object of interest and the prediction of the covariance based on a measurement value of the position of the object of interest in the X-ray image; and tracking the position of the object of interest.

9. The method of claim 8, wherein the controlling of the single collimator comprises determining a position and an area of the region in which the X-rays are radiated in correlation with the updated position of the object of interest and the updated covariance.

10. The method of claim 8, wherein the controlling of the single collimator comprises:

setting an oval region, in which the position of the object of interest is included, based on the updated position of the object of interest and the updated covariance; wherein the area of the X-ray radiation region corresponds to an area of the oval region.

11. The method of claim 8, further comprising, if the position of the object of interest is not measured in the X-ray image, repeatedly predicting the position of the object of interest and the covariance based on the predicted position of the object of interest and the predicted covariance.

12. The method of claim 11, wherein the controlling of the single collimator comprises correlating the position and the area of the region in which the X-rays are radiated with the predicted position of the object of interest and the predicted covariance.

13. The method of claim 11, wherein the controlling of the single collimator comprises:

setting an oval region, in which the position of the object of interest is included, based on the predicted position of the object of interest and the predicted covariance; wherein the area of the X-ray radiation region corresponds to an area of the oval region.

14. The method of claim 8, wherein the tracking of the position of the object of interest comprises tracking the position and speed of the object of interest in the ROI.

15. An X-ray imaging apparatus comprising:

an X-ray source;

a single collimator configured to adjust a radiation region of X-rays radiated by the X-ray source;

a processor configured to determine a region of interest (ROI) in an X-ray image, to track a position of an object of interest in the ROI, and to calculate covariance indicative of accuracy of the tracking; and a controller configured to control driving of the single collimator so that a position of a region in which X-rays are radiated follows the tracked position of the object of interest, and a size of the region in which the X-rays are radiated is correlated with the covariance.

16. The X-ray imaging apparatus of claim 1, further comprising at least one mask configured to reduce scattering of the X-rays.

17. The method of claim 8, further comprising reducing scattering of the X-rays via at least one mask.

18. The X-ray imaging apparatus of claim 15, further comprising at least one mask configured to reduce scattering of the X-rays.

* * * * *